US00PP22587P2

(12) United States Plant Patent
Harkness et al.

(10) Patent No.: US PP22,587 P2
(45) Date of Patent: Mar. 20, 2012

(54) FLORIBUNDA ROSE PLANT NAMED 'HARPAGEANT'

(50) Latin Name: *Rosa hybrida*
Varietal Denomination: HARpageant

(75) Inventors: Robert Harkness, Letchworth (GB); Philip Harkness, Letchworth (GB)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/925,119

(22) Filed: Oct. 14, 2010

(51) Int. Cl.
*A01H 5/00* (2006.01)

(52) U.S. Cl. ..... Plt./141

(58) Field of Classification Search ..... Plt./141, Plt./143, 146, 147
See application file for complete search history.

*Primary Examiner* — June Hwu
(74) *Attorney, Agent, or Firm* — McKee, Voorhees & Sease, P.L.C.

(57) ABSTRACT

A new variety of Floribunda rose suitable for garden decoration, having flowers of mango, peach & apricot blend coloration.

1 Drawing Sheet

Classification: The present invention relates to a new *Rosa hybrida* plant.

Variety denomination: The new plant has the varietal denomination 'HARpageant'.

BACKGROUND OF THE INVENTION

This invention relates to a new and distinct variety of Floribunda Rose. It has an undisseminated seedling of my creation as its seed parent with the following genetic origin (Queen Charlotte×Della Balfour) and as its pollen parent the variety known as 'SCRivluv' (not patented).

SUMMARY OF THE INVENTION

Among the features which distinguish the new variety from other presently available and commercial rose cultivars known to the inventor are the following combinations of characteristics: its red suffusion on the inner surface of the sepal that appears as the flower ages, its crenate petal margins mostly on the outermost petals, its very smooth and hairy rachis and petiole and its long lasting mango, peach & apricot blend flower coloration. The plant has an upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'HARpageant' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, an undisseminated seedling of my creation by the following combination of characteristics: whereas 'HARpageant' bears medium sized (about 7.0 to about 10.6 cm. in diameter) double flowers (about 20 to 32 petals), the undisseminated seedling bears significantly larger flowers (about 9.7 to about 12.4 cm. in diameter) with significantly heavier petalage (about 29 to 46 petals). The new variety bears flowers of mango, peach & apricot blend coloration, whereas the seed parent bears flowers of smoky burnished orange blend coloration.

The new variety may be distinguished from its pollen parent, 'SCRivluv' by the following combination of characteristics: whereas 'HARpageant' bears double flowers (about 20 to 32 petals) of mango, peach & apricot blend coloration, 'SCRivluv' bears single flowers of buttercup yellow coloration with significantly lesser petalage (5 petals). The new variety is classified as a floribunda rose with an upright medium height growing habit (about 100 to about 130 cm. in height), whereas the pollen parent is classified as a miniature rose with a significantly shorter bushy and rounded growing habit.

COMPARISON WITH THE CLOSEST COMMERCIALLY AVAILABLE CULTIVAR

The new variety may be distinguished from its closest commercially available cultivar, 'MElmonblan' (U.S. Plant Pat. No. 12,579) by the following combination of characteristics: whereas 'HARpageant' usually bears its flowers singly, sometimes in clusters of two to three or more per stem, 'MElmonblan' bears its flowers in significantly larger clusters of 6 to 15 flowers per stem. The new variety bears flowers of mango, peach & apricot blend coloration, whereas the closest commercially available cultivar bears flowers of marigold orange coloration. 'HARpageant' has an upright medium height growing habit (about 100 to about 130 cm. in height), whereas 'MElmonblan' has a significantly shorter growing habit (approximately 65 to 75 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of September. Phenotypic expression may vary with environmental, cultural and climatic conditions, as well as differences in conditions of light and soil.

FLOWER

The new variety usually bears its flowers singly, sometimes in clusters of two to three or more per stem. Flowers may be borne in regular rounded clusters on strong somewhat short stems (about 18 to about 58 cm.). Outdoors, the plant blooms abundantly and nearly continuously during the growing season. The flowers have a slight tea fragrance.

BUD

The peduncle is about 2.7 to about 4.6 cm. in length, of average caliper (about 0.2 to about 0.4 cm. in diameter), and usually erect. It is moderately rough, with many stipitate glands. Peduncle color is between 146C and 147C sometimes lightly suffused, especially on the side exposed to the sun, with between 187B and 183C.

Before the calyx breaks, the bud is about 1.1 to about 1.8 cm. in diameter at the widest point, about 1.3 to about 1.8 cm. in length, and pointed to moderately ovoid in shape. The surface of the bud bears some moderately long foliaceous appendages and very few stipitate glands, usually with stout much cut foliaceous parts extending beyond the tip of the bud about ½ or more of its length. Bud color is between 146B and 148C.

The sepals are about 2.6 to about 3.8 cm. in length and about 0.6 to about 1.0 cm. in width at the widest point. The outer surface color of the sepal is between 146B and 148C. The inner surface color of the sepal is near 138B broadly bordered by near 137B. After the sepals open, the inner surface color is often heavily suffused, especially on the area exposed to the sun, with between 187A and 187B. The inner surface of the sepal is covered with fine wooly tomentum; sepal margins are lined with few stipitate glands and many hairs.

The receptacle of the flower is of somewhat short length (about 0.3 to about 0.5 cm.) and moderately thin to average in caliper (about 0.5 to about 0.9 cm. in diameter). The receptacle is cup-shaped in form. Its surface is very smooth with moderately thin fleshy walls. The receptacle color is between 146C and 147C.

As the petals open (after the calyx breaks), the bud is about 1.5 to about 2.0 cm. in diameter at the widest point, about 1.7 to about 2.7 cm. in length, and somewhat pointed to moderately ovoid in form. The color of the under surfaces of the newly opened petals is between 45B and 42C sometime moderately suffused with near 187C. At the point where the petal attaches, there is a small zone of between 3B and 4A. The color at the base of the upper surfaces of the newly opened petals is between 23B and 21B gradually suffusing toward the edge of the petals with between 44B and 42C. At the point where the petal attaches, there is a somewhat large zone of between 6B and 5A.

BLOOM

When fully open, the bloom ranges from about 7.0 to about 10.6 cm. in diameter. Petalage is double with about 20 to 32 petals and about 1 to 6 petaloids irregularly arranged. When partially open, the bloom form is somewhat high centered to cupped, and the petals are tightly spiraled to cupped with petal edges moderately reflexed outward. When fully open, the bloom form is cupped, and the petals are loosely cupped to somewhat undulated with petal edges moderately reflexed outward and sometimes somewhat reflexed inward.

PETALS

The substance of the petals is moderately heavy and of medium to somewhat thick thickness, with upper surfaces moderately satiny and under surfaces matte to slightly shiny. The petals are about 3.1 to about 5.1 cm. in length and about 3.0 to about 5.7 cm. in width at the widest point. Petal margins are usually entire, often moderately crenate mostly on the outermost petals.

The outer petals are broadly obovate in shape with rounded apices.

The inner petals are obovate in shape with rounded apices.

Petaloids are about 1.4 to about 3.7 cm. in length and about 0.6 to about 2.4 cm. in width at the widest point. Petaloids are irregularly shaped somewhat obovate to subulate with rounded apices.

NEWLY OPENED FLOWER

The under surface color of the outer petals is between 39B and 31B often lightly suffused with near 53C. At the point where the petal attaches, there is a medium size zone of between 5C and 4B. The color at the base of the upper surfaces of the outer petals is between 23C and 21B gradually suffusing toward the edge of the petals with between 37B and 24C often moderately blushed with between 53C and 53D. At the point where the petal attaches, there is a large zone of between 9B and 12B.

The under surface color of the intermediate and inner petals is between 39B and 31B often lightly suffused with near 53C. The color at the base of the upper surfaces of the intermediate and inner petals is between 23C and 21B gradually suffusing toward the edge of the petals with between 32D and 24C.

The under and upper surface colors of the petaloids are similar in coloration to the upper and under surfaces of the intermediate and inner petals.

The general tonality of the newly opened flower is between 23C and 21B at the base gradually suffusing toward the edge of the petals with between 32D and 24C.

THREE-DAY-OLD FLOWER

The under surface color of the outer petals is between 43C and 31C often lightly suffused with near 61B. At the point where the petal attaches, there is a medium size zone of between 5C and 4B. The color at the base of the upper surfaces of the outer petals is between 17D and 21C gradually suffusing toward the edge of the petals with between 37B and 26C often moderately blushed with near 61B. At the point where the petal attaches, there is a large zone of between 9B and 12B.

The under surface color of the intermediate and inner petals is between 43C and 31C often lightly suffused with near 53C. The color at the base of the upper surfaces of the intermediate and inner petals is between 17D and 21C gradually suffusing toward the edge of the petals with between 37B and 26C often moderately blushed with near 60B.

The under and upper surface colors of the petaloids are similar in coloration to the upper and under surfaces of the intermediate and inner petals.

The general tonality of the three-day-old flower is between 17D and 21C at the base gradually suffusing toward the edge of the petals with between 37B and 26C often moderately blushed with near 60B.

On the spent bloom, the petals usually drop off cleanly.

In September in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 110) and are arranged regularly about the pistils; a few are mixed with petaloids. The filaments are of medium length (about 0.6 to about 1.3 cm.) most with anthers. Filaments are between 12A and 13A in color often lightly suffused with between 53B and 53C. The anthers are somewhat small for the class and all open approximately at the same time. Anther color when immature is near 22A on the external part and near 13D on the internal part. Anther color at maturity is near 161C on the external part and near 200B on the internal part. Pollen is abundant and between 23B and 24B in color.

FEMALE REPRODUCTIVE ORGANS

Pistils vary in number (average about 80). The styles are uneven, moderately short in length (about 0.4 to about 0.8 cm.), moderately thin in caliper, and columnar to somewhat loosely separated. Stigma color is between 10A and 11A. Style color is between 1D and 154D sometimes lightly suffused with 53A and 53B. Ovaries are usually all enclosed in the calyx.

Hips are of moderately short length (about 0.8 to about 1.5 cm.), moderately globular in form and flat at the top, and between 28B and 30B in color when ripe. The hip surface is very smooth with moderately thick dry fleshy walls. The sepals are somewhat permanent, and usually straight in shape.

The seeds are irregularly rounded, smooth in texture, approximately 13 to about 22 per hip, about 0.3 to about 0.7 cm. in diameter at the widest point and between 161B and 164C in color.

FOLIAGE

The compound leaves are usually comprised of three to five leaflets and are borne abundantly. The five-leaflet leaves are about 7.7 to about 11.9 cm. in length and about 5.2 to about 9.2 cm. in width at the widest point, moderately leathery to somewhat crisp in texture, and moderately glossy in finish on the upper side and matte to slightly shiny in finish on the under side. The terminal leaflets are about 3.5 to about 6.0 cm. in length and about 2.0 to about 4.1 cm. in width at the widest point, shaped ovate with acute to somewhat acuminate apices and rounded bases. Their margins are simply serrate.

The upper surface color of the mature leaf is between 139A and 147A. The under surface color of the mature leaf is between 147B and 138B. The upper surface color of the young leaf is between 137C and 147B, often moderately suffused with between 187B and 187A. The under surface color of the young leaf is between 146B and 147C, often moderately suffused with between 187B and 187A.

The rachis is average in caliper and very smooth. The upper side is deeply grooved with many hairs and some stipitate glands on the edges of the grooves. The under side of the rachis is very smooth with some hairs. The rachis color is near 146D on the under side and near 146B on the upper side often heavily suffused on the young leaves with between 187A and 187B.

The stipules are about 1.2 to about 1.8 cm. in length and moderately wide (about 0.6 to about 1.0 cm.) with somewhat long straight points that usually turn out at an angle of more than 45 degrees and sometimes recurve toward the stem. The stipule color is between 146B and 137C.

The petiole is average in caliper and very smooth. The upper side is deeply grooved with many hairs and some stipitate glands on the edges of the grooves. The under side of the petiole is very smooth with some hairs. The petiole is about 0.4 to about 1.0 cm. in length and about 0.1 to about 0.15 cm in width at the widest point. The petiole color is near 146D on the under side and near 146B on the upper side often heavily suffused on the young leaves with between 187A and 187B.

The plant displays an above average degree of resistance to powdery mildew and black spot and a below average resistance to rust as compared to other commercial varieties grown under comparable conditions in Pomona, Calif. The plant's winter hardiness and drought/heat tolerance are yet to be determined.

GROWTH

The plant has an upright medium height growing habit (about 100 to about 130 cm. in height and about 50 to about 65 cm. spread at the widest point), with full branching. It displays moderately vigorous growth and the canes are of medium to somewhat light caliper for the class (about 0.9 to about 1.5 cm. in width at the widest point).

The color of the major stems is between 148A and 152A. They bear some large prickles that are about 0.7 to about 0.9 cm. in length. The large prickles are angled slightly downward with a medium length somewhat narrow oval base; prickle color is between 165B and 166C. The major stem bears few small prickles of similar shape and coloration.

The color of the branches is between 146B and 148A. They bear some large prickles which are of similar size and shape to the large prickles on the major stems; prickle color is between 153A and 152D sometimes lightly suffused with between 183D and 187B. The branches bear few small prickles of similar shape and coloration.

The color of the new shoots is between 146C and 147B. They bear some large prickles which are of similar size and shape to the large prickles on the major stems; prickle color is between 153A and 152D usually moderately suffused with between 187C and 187B. The shoots bear few small prickles of similar shape and coloration.

I claim:

1. A new and distinct Floribunda rose plant of the variety substantially as described and illustrated herein.

* * * * *

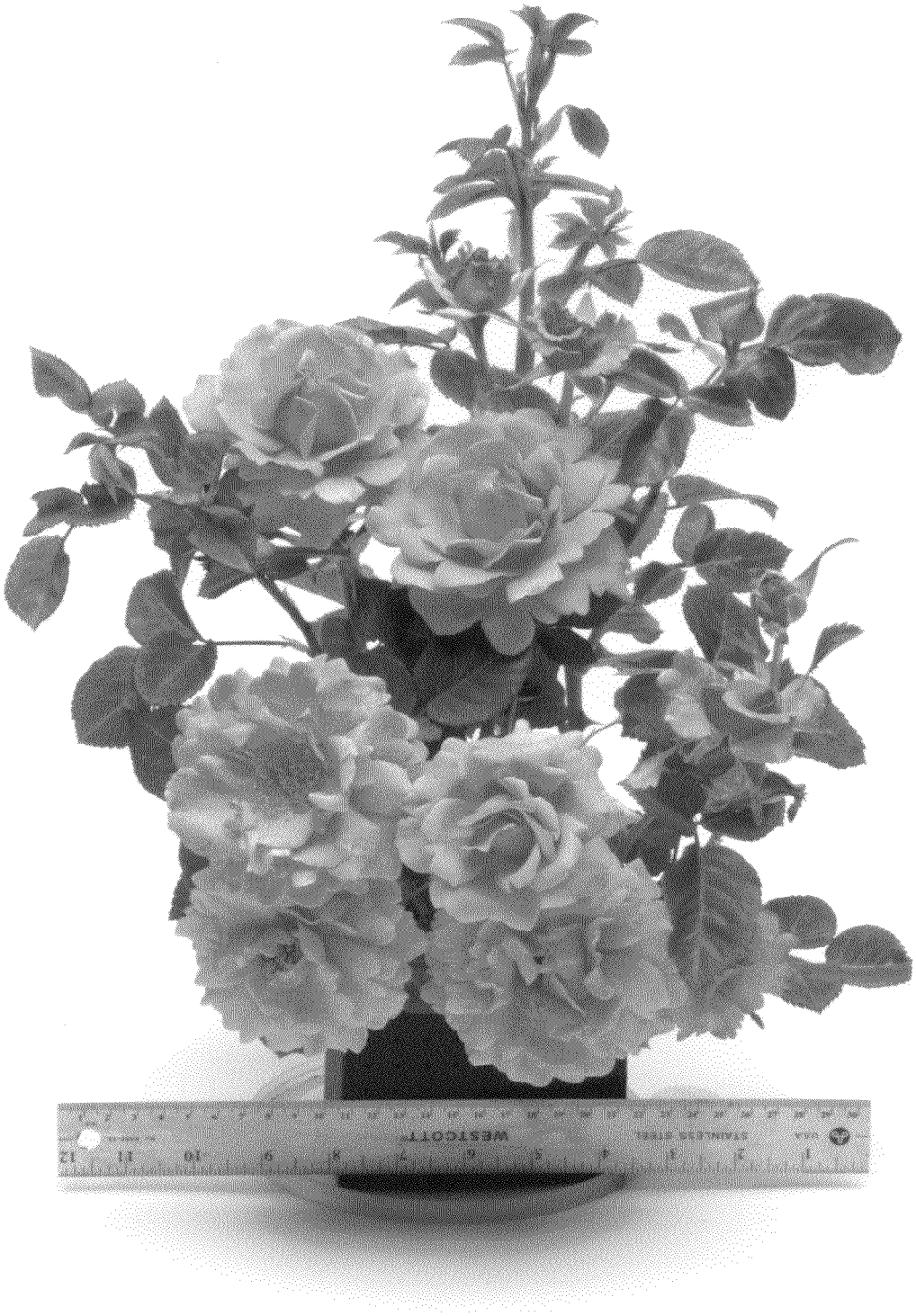
WESTCOTT
STAINLESS STEEL